United States Patent
Kawaguchi et al.

(10) Patent No.: US 6,433,054 B1
(45) Date of Patent: Aug. 13, 2002

(54) GEL-FORM PRESSURE-SENSITIVE ADHESIVE, AND ADHESIVE MATERIAL AND ADHESIVE MEDICINAL PREPARATION BOTH CONTAINING THE SAME

(75) Inventors: Takeyuki Kawaguchi; Hiroyoshi Minematsu; Susumu Maruo; Hiroaki Kuwahara; Takanori Miyoshi; Michio Iwai, all of Iwakuni (JP)

(73) Assignee: Teijin Limited, Osaka (JP)

( * ) Notice: Subject to any disclaimer, the term of this patent is extended or adjusted under 35 U.S.C. 154(b) by 0 days.

(21) Appl. No.: 09/508,765

(22) PCT Filed: Sep. 11, 1998

(86) PCT No.: PCT/JP98/04127

§ 371 (c)(1),
(2), (4) Date: Mar. 16, 2000

(87) PCT Pub. No.: WO99/14283

PCT Pub. Date: Mar. 25, 1999

(30) Foreign Application Priority Data

Sep. 16, 1997 (JP) .............................. 9-250629

(51) Int. Cl.$^7$ .......................... C08K 5/09; C08K 5/101; C09J 167/00; C09J 175/14; C09J 177/00
(52) U.S. Cl. ...................... 524/315; 524/318; 524/322; 524/377; 524/386; 524/387
(58) Field of Search ................. 524/315, 318, 524/322, 377, 386, 387

(56) References Cited

U.S. PATENT DOCUMENTS 5,270,358 A   12/1993   Asmus ........................ 524/55

FOREIGN PATENT DOCUMENTS

| EP | 0 763 358 A1 | 3/1997 | ............ A61K/9/70 |
| JP | 4-297416 | 10/1992 | ............ A61K/9/70 |
| JP | 5-503863 | 6/1993 | ............ A61L/15/16 |
| JP | 8-245936 | 9/1996 | ............ C09J/11/08 |
| JP | 9-110682 | 4/1997 | ............ A61K/9/70 |
| JP | 9-132525 | 5/1997 | ............ A61K/9/70 |
| JP | 9-301854 | 11/1997 | ............ A61K/9/70 |

OTHER PUBLICATIONS

Patent Abstracts of Japan, vol. 010, No. 071, for JP 60–208912 (Oct. 21, 1985).
Pub Med, National Library of Medicine, Biomed Mater Res Nov. 1988; 22(11):1023–32, Hydrogels For Buccal Drug Delivery: Properties Relevant For Muco–Adhesion, de Vries ME, Bodde HE, Busscher HJ, Junginger HE; PMID: 3241007 (PubMed—indexed for MEDLINE) (Abstract).
Pub Med, National Library of Medicine, J AM Acad Dermatol Mar. 1989; 20(3):447–53, Easier Patch Testing With TRUE Test, Fischer T, Maibach HI., PMID:2918115 (PubMed—indexed For MEDLINE) (Abstract).
Pub Med, National Library of Medicine, Burns Aug. 1991; 17(4):313–9, Adhesive Contact Media—An Update On Graft Fixation And Burn Scar Management, Davey RB, Wallis KA, Bowering K., PMID:1930667 (PubMed—indexed For MEDLINE) (Abstract).
PubMed, National Library of Medicine, Biomaterials Jan. 1995; 16(2):145–8, Development And In Vitro Evaluation of Chitosan–Based Transdermal Drug Delivery Systems For The Controlled Delivery of Propranolol Hydrochloride, Thacharodi D., Rao KP., PMID: 7734649 (PubMed—indexed for MEDLINE) (Abstract).
PubMed, National Library of Medicine, Biomaterials May 1995; 16(8):617–24, In Vitro Assessment Of Bioadhesion For Periodontal And Buccal Drug Delivery, Needleman IG, Smales FC, PMID: 75486123 (PubMed—Indexed for MEDLINE) (Abstract).
PubMed, National Library of Medicine, J Steroid Biochem Mol Biol Jun. 1995; 53(1–6):247–51, Transdermal Application of Steroid Hormones For Contraception, Sitruk–Ware R. (Abstract).
PubMed, National Library of Medicine, Pharm Res Feb. 1996:; 13(2):279–83, The Effects Of Ageing On the Rheological, Dielectric And Mucoadhesive Properties Of Poly(acrylic acid) Gel Systems, Tamburic S, Craig DQ, PMID:8932449 (PubMed—indexed for MEDLINE) (Abstract).
PubMed, National Library of Medicine, Biomaterials Jul. 1996; 17(14):1387–91, Rapidly Curable Biological Glue Composed Of Gelatin And Poly(L–Glutamic Acid). Otani Y, Tabata Y. Ikada Y., PMID:8830964(PubMed—indexed for MEDLINE) (Abstract).
PubMed, National Library of Medicine, J. Biomater Sci Polym Ed 1996;7(12):1055–64, Mucoadhesive Poly (vinyl alcohol) Hydrogels Produced By Freezing/Thawing Processes: Applications In The Development Of Wound Healing Systems, Mongia NK, Anseth KS, Peppas NA., PMID:8880437 (PubMed—indexed for MEDLINE) (Abstract).

*Primary Examiner*—Peter Szekely
(74) *Attorney, Agent, or Firm*—Sughrue Mion, PLLC

(57) ABSTRACT

The gel adhesive of the present invention contains an elastomer component (A), a self-adhesive polymer component (B) compatible with the elastomer component (A), and a liquid component (C) compatible with the elastomer component (A) and the self-adhesive polymer (B), the liquid component (C) being held in a mixture of the elastomer component (A) and the self-adhesive polymer (B) without exuding, to form as a whole, a gel, and is useful for forming a self-adhesive layer of an adhesive material or a pharmaceutical-containing self-adhesive layer of an adhering pharmaceutical preparation, which layer is capable of being firmly adhered to a surface to be adhered, and particularly a body skin surface, and of being easily removed therefrom without leaving a portion of the layer on the adhered surface.

4 Claims, No Drawings

GEL-FORM PRESSURE-SENSITIVE ADHESIVE, AND ADHESIVE MATERIAL AND ADHESIVE MEDICINAL PREPARATION BOTH CONTAINING THE SAME

TECHNICAL FIELD

The present invention relates to a gel adhesive, an adhesive material containing that gel adhesive, and an adhering pharmaceutical preparation. More particularly, the present invention relates to a gel adhesive that is highly adhesive and is easily removable, a removable adhesive material having an adhesive surface that contains this gel adhesive that is used in applications such as protection of body skin, and an adhering pharmaceutical preparation that has an adhesive layer containing a pharmaceutical and the above-mentioned gel adhesive and can be removably adhered to the surface of body skin.

BACKGROUND ART

In recent years, various types of percutaneously absorbed tape preparations have been developed for administration of a drug into the body through the surface of the skin. Normally, such tape preparations preferably have necessary adhesive strength to prevent removal from the surface of the skin to which they are adhered, while also having an ease of removal to the extent that the skin surface (corneal layer) is not damaged when the tape preparation is removed after use.

In the case of rubber-based adhesives of the prior art, the addition of a liquid component such as liquid paraffin is used as means of preventing damage to the corneal layer of body skin during removal. However, in the case of using the above-mentioned adhesive of the prior art, it is necessary to add low molecular weight additives such as antioxidants and stabilizers, as well as adhesion-enhancing resins. Thus, even if it were possible to suppress removal of the corneal layer, it was difficult to suppress skin irritation.

Japanese Unexamined Patent Publication No. 60-208912 discloses a process for improving the stability of an adhesive by using polyester elastomer instead of natural rubber or synthetic rubber. In this, process, although the addition of antioxidant and stabilizer can be eliminated, it is necessary to add an adhesion-enhancing resin having a relatively low molecular weight (number average molecular weight<2000). Thus, skin irritation caused by this adhesion-enhancing resin could not be avoided.

In addition, Japanese Unexamined Patent Publication No. 62-230715 discloses a process for reducing skin irritation by using a base that reduces the adhesive strength (<300 g/12 mm) while not containing an adhesion enhancer by blending a non-adhesive thermoplastic urethane copolymer into an adhesive thermoplastic acrylic copolymer. In this process, however, since the adhesive strength of an adhesive resin is lowered by blending in a copolymer substantially without adhesive strength, and although this adhesive has the necessary adhesive strength to prevent removal from the contact surface of the skin, it is difficult to simultaneously demonstrate an ease of removal to the extent that the skin surface (corneal layer) is not damaged when the adhesive is removed after use.

Japanese Unexamined Patent Publication No. 3-220120 discloses an acrylic gel adhesive material in which a crosslinked gel layer, containing an acrylate ester polymer and a liquid component that is compatible with this polymer, is formed on at least one side of a support. According to this publication, since the gel adhesive is able to contain a large amount of a liquid component, it is possible to achieve a better balance between adhesive strength and removal ease than in non-crosslinked adhesives of the prior art, thereby making it possible to reduce removal of the corneal layer. In the gel adhesive of this publication, however, since the cohesive force of the adhesive is augmented, it is necessary to crosslink the acrylic acid units contained in the acrylate ester polymer in a chemical reaction with a low molecular weight crosslinking agent such as an alkolate of a polyvalent metal such as aluminum or titanium or a trifunctional isocyanate. In typical polymer reactions, since it is extremely difficult to achieve a reaction rate of 100%, and normally unreacted reaction components remain in the reaction system and, when these reaction products are used in a skin adhesion material, there is the risk of unreacted reaction components being percutaneously absorbed into the blood.

Japanese Unexamined Patent Publication No. 4-230212 discloses a process that allows a plastic active substance like a permeability promoter to be retained in an adhesive at high concentration without requiring additional chemical modification of a polyacrylate ester adhesive, wherein a polymethacrylatelester polymer, which although itself is not adhesive, but has extremely satisfactory film forming properties, is added to polyacrylate ester adhesive. However, in the case of adding a non-self-adhesive, film-forming polymethacrylate ester polymer to an adhesive polymer, although the cohesive strength of the adhesive polymer can be increased, the flexibility of the adhesive polymer (having a glass transition temperature of minus several tens °C.) ends up decreasing. Consequently, according to the process described in the above-mentioned publication, it is difficult to obtain an adhesive that simultaneously is easy to remove, to an extent that the skin surface (corneal layer) is not damaged, when it is removed following use. Moreover, since aluminum or titanium and so forth is added as a non-plastic assistant in all of the embodiments of this process, problems arise that are similar to those of the process described in the above-mentioned Japanese Unexamined Patent Publication No. 3-220120.

DISCLOSURE OF THE INVENTION

The object of the present invention is to provide a gel adhesive having removable adhesive strength and strong cohesive strength, an adhesive material containing that adhesive, and an adhering pharmaceutical preparation.

In addition, another object of the present invention is to provide a gel adhesive that stably retains its adhesive state to body skin, can be easily removed without damaging body skin as necessary, and does not remain adhered on the body skin during removal, an adhesive material containing that adhesive having high moisture permeability and able to protect body skin while not causing irritation or rash of body skin, and an adhering pharmaceutical preparation that allows a desired pharmaceutical to be absorbed into the body through body skin.

The above-mentioned objects can be achieved by the gel adhesive, adhesive material containing that gel adhesive, and adhering pharmaceutical preparation of the present invention.

The gel adhesive of the present invention contains an elastomer component (A), a self-adhesive polymer component (B) compatible with said elastomer component (A), and a liquid component (C) compatible with said elastomer component (A) and said self-adhesive polymer component (B) to form an adhesive gel; said liquid component (C) being held in a mixture of said elastomer component (A) and said adhesive polymer (B) without exuding.

In the gel adhesive of the present invention, the mixing weight ratio (B)/(A) of said self-adhesive polymer component (B) to said elastomer component (A) is preferably from 1.0:2.0 to 1.0:0.1, and the mixing weight ratio [(A)+(B)]/(C) of the total weight of said elastomer component (A) and said self-adhesive polymer component (B) to said liquid component (C) is preferably from 1.0:0.1 to 1.0:2.0.

In the gel adhesive of the present invention, said elastomer component (A) preferably contains at least one type selected from the group consisting of polyurethane elastomer, polyester elastomer and polyamide elastomer, said self-adhesive polymer component (B) preferably contains at least one type selected from the group consisting of acrylate ester polymer and vinyl acetate polymer, and said liquid component (C) preferably contains at least one type selected from the group consisting of liquid higher fatty acid ester, liquid higher fatty acid, liquid polyvalent alcohol and liquid polyvalent alcohol derivative.

The adhesive material of the present invention is formed and supported on a support and has a self-adhesive layer containing the above-mentioned, gel adhesive of the present invention.

In the above-mentioned adhesive material, a functional substance such as colorant, fragrance or refrigerant may be mixed into the above-mentioned gel adhesive.

The adhering pharmaceutical preparation of the present invention has a support, and a self-adhesive layer formed and supported on this support and containing the above-mentioned gel adhesive of the present invention and a pharmaceutical.

BEST MODE FOR CARRYING OUT THE INVENTION

The gel adhesive of the present invention contains an elastomer component (A), self-adhesive polymer component (B) and liquid component (C).

The elastomer component (A) used in the present invention preferably contains at least one compound, selected from the compounds indicated below, that is compatible with liquid component (C) and has high moisture permeability and stability.

(1) Aliphatic and aromatic polyurethane elastomers, examples of which include aliphatic and aromatic polyether urethane, polyether polyurea, polyether polyurethane urea, polyether ester polyurethane, polyether ester polyurea and polyether ester polyurethane urea elastomers.

(2) Aliphatic and aromatic polyester elastomers, examples of which include aliphatic and aromatic polyether ester and polyester elastomers.

(3) Aliphatic and aromatic polyamide elastomers, examples of which include aliphatic and aromatic polyether polyamide and polyester polyamide elastomers.

Those above-mentioned elastomer compounds used for elastomer component (A) are used preferably in the present invention by having a high content retention ability for liquid component (C) and superior solubility in solvent, etc. More specifically; aliphatic and aromatic polyurethane elastomers are preferably selected from polyurethanes obtained using at least one type of isocyanate such as diphenylmethane diisocyanate, isophorone diisocyanate and dicyclohexylmethane diisocyanate as its isocyanate component, and using at least one type of diol such as polyoles having a number average molecular weight of 400–3000 such as polytetramethylene glycol, hexanediol polycarbonate and polytetrahydrofuran, along with butanediol, hexanediol and octanediol as its diol component. In addition, these elastomers may be used alone or as a mixture of two or more types.

The self-adhesive polymer component (B) is able to be compatible with the above-mentioned elastomer component (A), and more specifically, contains one type or two or more types of the polymers selected from the group consisting of polyacrylate ester-based adhesive polymer, polyvinylacetate-based adhesive polymer, polyvinyl ether-based adhesive polymer and silicon-based adhesive polymer.

In particular, polyacrylate ester-based adhesive polymer and polyvinyl acetate-based adhesive polymer are preferably used in the present invention as a result of having the advantage of being able to retain a larger amount of liquid component (C).

Polyacrylate ester-based adhesive polymers that are used as self-adhesive polymer component (B) in the present invention are preferably alkyl(meth)acrylate ester-acrylic acid copolymers that contain 50 wt % or more of alkyl(meth)acrylate ester having 2–20 carbon atoms, and 10 wt % or less of acrylic acid. Examples of alkyl(meth)acrylate esters having 2–20 carbon atoms include ethyl(meth)acrylate, butyl(meth)acrylate, pentyl(meth)acrylate, hexyl(meth)acrylate, heptyl(meth)acrylate, octyl(meth)acrylate, 2-ethylhexyl(meth)acrylate, nonyl(meth)acrylate, decyl(meth)acrylate, dodecyl(meth)acrylate, hexadecyl(meth)acrylate and octadecyl(meth)acrylate. In particular, copolymers having for their main component 2-ethylhexyl(meth)acrylate are superior in terms of adhesive strength and cohesive strength, and are preferably used in the present invention. A monomer other than the above-mentioned alkyl(meth)acrylate esters can be copolymerized as necessary with the above-mentioned alkyl(meth)acrylate ester and acrylic acid. Examples of these comonomers include vinyl ethers such as butylvinyl ether and methylvinlyl ether, as well as vinyl acetate, vinyl propionate, vinylpyrrolidone, vinylimidazole, vinylcaprolactam, maleic anhydride, itaconic acid, maleic acid, hydroxyethylacrylate, hydroxypropylacrylate, acrylamide, dimethylacrylamide and acrylonitrile. These comonomers are subjected to copolymerization under conditions which does not impair adhesive strength or cohesive strength of the resulting adhesive.

In addition, in the case of polyvinyl acetate-based self-adhesive polymers, copolymers containing 50 wt % or more of vinyl acetate and 10 wt % or less of acrylic acid have superior adhesiveness and cohesive strength, and are preferably used in the present invention. Other copolymerizable comonomers may be copolymerized with the above-mentioned vinyl acetate and acrylic acid. Examples of these comonomers include alkyl(meth)acrylates such as methyl(meth)acrylate, ethyl(meth)acrylate, butyl(meth)acrylate and pentyl(meth)acrylate, hexyl(meth)acrylate, 2-ethylhexyl(meth)acrylate and octyl(meth)acrylate; vinyl ethers such as butylvinyl ether and methylvinyl ether; as well as vinyl propionate, vinylpyrrolidone, vinylimadazole, vinylcaprolactam, maleic anhydride, itaconic acid, maleic acid, hydroxyethylacrylate, hydroxypropylacrylate, acrylamide, dimethylacrylamide and acrylonitrile. These comonomers are supplied to copolymerization within a range that does not impair the adhesive strength or cohesive strength of the adhesive.

Moreover, examples of polyvinyl ether-based self-adhesive polymers include polyvinylmethyl ether, polyvinylethyl ether, and polyvinylisobutyl ether. In particular, polyvinylmethyl ether is used preferably in the present invention due to its superior adhesive strength.

Moreover, examples of silicon-based self-adhesive polymers include polydimethylcyclohexane, polydimethylphenylsiloxane and polydimethylsiloxane polyethylene glycol copolymer. In particular, polydimethyldiphenylsiloxane elastomer is used preferably in the present invention as a result of having excellent compatibility with liquid component (C) and excellent adhesiveness as well as having the advantage of low cost.

The liquid component (C) used in the present invention can be compatible with elastomer (A) and self-adhesive polymer (B) of the present invention, and this liquid component (C) is held in a mixture of the above-mentioned elastomer component (A) and self-adhesive polymer component (B) without being exuded from the mixture to form an adhesive gel.

This liquid component (C) is preferably a liquid at room temperature, specific examples of which include polyvalent alcohols such as propylene glycol, hexanetriole, glycerin, polyethylene glycol, polypropylene glycol and poly (oxyethylene-oxypropylene) glycol; polyvalent alcohol derivatives such as monoacetine, triacetine, triisooctanoate glycerin, sorbitan monocaprylate and sorbitan monooleate; higher fatty acid esters such as isopropyl myristate, isooctyl palmitate, ethyl oleate and diethyl sebacate; higher fatty acids such as linolenic acid, linoleic acid, oleic acid and capric acid; oils such as olive oil and castor oil; fatty acid esters such as diethyl phthalate and diisopropyl adipate; aprotic polar organic compounds such as dimethylsulfoxide, dimethylformamide, dimethylacetoamide and N-methylpyrrolidone; surfactants such as lauryl amide, dimethyldecylsulfoxide and dodecylpyrrolidone; and hydrocarbons such as liquid paraffin. These may be used alone or as a mixture of two or more types.

Preferable examples of the above-mentioned compounds useful as liquid component (C) of the present invention include higher fatty acid esters such as isopropyl myristate, isooctyl palmitate and ethyl oleate, as well as higher fatty acids such asllinolenic acid, linoleic acid and oleic acid, and are preferable as a result of being effective in improving the adhesive strength and ease of release of the resulting adhesive as well as the percutaneous absorption of the drug. In addition, since polyvalent alcohols such as propylene glycol, hexanetriol, glycerin, polyethylene glycol, polypropylene glycol and poly(oxyethylene-oxypropylene) glycol, as. well as polyvalent alcohol derivatives such as monoacetine, triacetine, triisooctanoate glycerin, sorbitan monocaprylate and sorbitan monooleate have high moisture permeability, they are superior in terms of suppressing skin irritation, and are used preferably as liquid component (C).

The above-mentioned elastomer component (A), self-adhesive polymer component (B) and liquid component (C) are suitably selected in consideration of demonstrating suitable adhesive to the adhering surface such as skin, and in the case of composing an adhesive, to the ease by which the creep characteristics of the self-adhesive layer are controlled to a proper degree.

When one type or two or more types of elastomers selected from polyurethane elastomers, polyester elastomers and polyamide elastomers are used for the above-mentioned elastomer component (A), one type or two or more types of self-adhesive polymer selected from the group consisting of polyacrylester-based self-adhesive polymers and polyvinylacetate-based self-adhesive polymers are selected for the above-mentioned self-adhesive polymer component (B), and one type or two or more types of compounds selected from the group consisting of higher fatty acid esters, higher fatty acids, polyvalent alcohols and polyvalent alcohol derivatives are used for the above-mentioned liquid component (C), the resultingigel adhesive is preferable in terms of having high adhesiveness and cohesive strength and causing little of the skin.

As a particularly preferable combination of components (A), (B) and (C) of the gel adhesive of the present invention, when polyurethane elastomer is used for elastomer component (A), alkyl(meth)acrylate ester copolymer polyacrylate ester-based self-adhesive polymer having 2-ethylhexylacrylate for its main ingredient and containing 10 wt % or less of acrylic acid is used for self-adhesive polymer component (B), and a high fatty acid ester such as isopropyl myristate and/or a polyvalent alcohol such as poly(oxyethyleneoxypropylene)glycol is used for the above-mentioned liquid component (C), a preferable gel adhesive is obtained having high adhesiveness and cohesive strength that causes little skin irritation.

In the present invention, elastomer component (A), self-adhesive polymer component (B) and liquid component (C) are mixed at a ratio to form an adhesive gel to an extent that liquid component (C) does not exude from the mixture.

A gel adhesive prepared in this suitable blending ratio has suitable adhesive strength required to prevent removal from, for example, the skin contact surface, and ease of removal to an extent that does not damage the adhered surface, and particularly the surface of the skin, when removed after use, and moreover, is a safe adhesive that leaves little adhesive on the adhered surface due to its high cohesive strength.

In the present invention, a gel adhesive from which there is exudation of liquid component (C) refers to a gel adhesive that adheres to a Bakelite plate in which liquid component (C) and/or self-adhesive polymer component (B) do not remain adhered to the Bakelite plate after removal when this Bakelite plate is subjected to a 180 degree removal force test as will be described later.

The above-mentioned gel adhesive can be formed by suitably selecting the types and blended amounts of elastomer component (A), self-adhesive polymer component (B) and liquid component (C). In order to obtain a preferable gel adhesive, the blending weight ratio of self-adhesive polymer component (B) and elastomer component (A) is preferably 1.0:2.0 to 1.0:0.1, and the blending weight ratio of the total content of self-adhesive polymer component (B) and elastomer component (A) to liquid component (C) is preferably 1.0:0.1 to 1.0:2.0. The use of these ratios provides a suitable adhesive strength required to prevent removal from the adhered surface, and particularly the skin contact surface, as well as ease of removal to an extent that does not damage the adhered surface, and particularly the surface of the skin, during removal after use. The suitable tack in this case (as determined by a measurement method to be described later) is preferably 150 to 500 g/5.1 mm$\Phi$, and a low 180 degree removal force for realizing ease of removal after use (as determined by a measurement method to be described later) is preferably 40 to 300 g/12 mm.

In the production of an adhesive material using the gel adhesive of the present invention, after mixing and dissolving the above-mentioned elastomer component (A), self-adhesive polymer component (B) and liquid component (C) in a common solvent and in suitable blending ratios, this solution is coated onto one side of a substrate (or mold release material) followed by removal of the solvent by drying treatment to form a self-adhesive layer containing gel adhesive. The thickness of the self-adhesive layer formed in this manner is preferably controlled normally within the range of 20 μm to 200 μm, and preferably 30 μm to 100 μm, according to the drug used in the case of, for example, mixing the gel adhesive with a pharmaceutical.

The adhesive material of the present invention has a support and a self-adhesive layer that is formed on this support and contains the gel adhesive of the present invention. The support and self-adhesive layer may be laminated either directly or indirectly, and lamination can be performed by a known method such as coating the gel adhesive or its solution directly onto the support using, for example, a coater, or transferring the self-adhesive layer onto the support.

The support used for the adhesive material of the present invention should allow formation of the above-mentioned self-adhesive layer, and have self-shape retention. The support used in an adhering pharmaceutical preparation of the present invention should be able to be used in applications in which the adhering pharmaceutical preparation is adhered to the skin surface and the drug is allowed to be absorbed by the body by permeating through the skin, or in applications such as protection of the skin surface, and there are no particular restrictions on its material, dimensions or shape. The support can be selected from polymer films such as polyester, polyolefin and cellulose ester films; woven fabrics, knitted fabrics and non-woven fabrics composed of fibers such as polyester, polyolefin, cellulose ester, polyurethane and polyamide fibers; paper sheets, porous films composed of polyester, polyolefin, cellulose ester, polyurethane and polyamide; and, laminates composed of combinations of two or more of these types. The thickness of the support is set normally within the range of 100 μm to 2000 μm, and preferably 200 μm to 1000 μm according to the type of adhesive material.

In the adhesive material of the present invention, the self-adhesive layer may be composed of the gel adhesive of the present invention only, or functional substances may be mixed into the gel adhesive of the present invention. Examples of functional substances that can be contained in addition to the pharmaceuticals to be described later include colorant (dye, pigment), fragrance and refrigerant according to the application of the adhesive material.

Although the amount of functional substance added can be suitably set according to the type and purpose of use, it is generally preferable that the amount added be 0.1 to 10 wt % relative to the total weight of the self-adhesive layer.

The adhering pharmaceutical preparation of the present invention has a support and a self-adhesive layer formed on that support and containing the above-mentioned gel adhesive of the present invention and a pharmaceutical. Namely, in the adhering pharmaceutical preparation of the present invention, a pharmaceutical is contained in its self-adhesive layer. Although there are no particular restrictions on the pharmaceutical contained, it is preferable to use a lipid-soluble pharmaceutical able to dissolve in the gel adhesive or liquid component (C) of the present invention. The following lists examples of such pharmaceuticals.

(1) Corticosteroids:
Hydrocortisone, prednisolone, parametasone, beclomethasone propionate, flumetasone, betametasone, betametasone valerate, dexametasone, triamcinolone, triamcinolone acetonide, fluocinolone acetonide, fluocinolone acetonide acetate and clobetasol propionate.

(2) Resolving Analgesics:
Indometacin, ketoprofen, acetaminophen, mefenamic acid, flufenamic acid, diclofenac, diclofenac sodium, alclofenac, oxyphenbutazone, phenylbutazone, ibuprofen, flurbiprofen, salicylic acid, methyl salicylate, 1-menthol, camphor, sulindac, tolmetin sodium, naproxen and fenbufen.

(3) Soporific Analgesics:
Phenobarbital, amobarbital, cyclobarbital, triazolam, nitrazepam, flunitrazepam, lorazepam and haloperidol.

(4) Tranquilizers:
Fluphenazine, theoridazin, diazepam, fludiazepam, flunitrazepam and chlorpromazine.

(5) Antihypertensives:
Clonidine, clonidine hydrochloride, pindolol, propranolol, propranolol hydrochloride, bifuranol, nivadipine, nimodipine, lofedixine, indenolol, nitrendipine, nipradilol, bucumolol and nifedipin.

(6) Depressor Diuretics:
Hydrothiazide, bendroflumethiazide and cyclopenthiazide.

(7) Antibiotics:
Penicillin, tetracycline, oxytetracycline, fradiomycin sulfate, erythromycin and chloramphenicol.

(8) Anesthetics:
Lidocaine, dibucaine hydrochloride, benzocaine and aminobenzoate ester.

(9) Antibiotic Substances:
Benzalkonium chloride, nitrofurazone, nystatin, acetosulfamide and clotrimazole.

(10) Antimycotics:
Pentamycin, amphotericin B, pyrollnitrin and clotrimazole.

(11) Vitamins:
Vitamin A, vitamin E, vitamin $K_1$, ergocalciferol, cholecalciferol, octothiazine and riboflavin butyrate ester.

(12) Antiepileptics:
Nitrazepam, meprobamate and clonazepam.

(13) Coronary Vasodilators:
Nitroglycerin, nitroglycol, isosorbide dinitrate, erythritol tetranlitrate, propatyl nitrate, dipyridamole and morisidomine.

(14) Antihistamines:
Diphenhydramine hydrochloride, chlorpheniramine and diphenylimidazole.

(15) Antitussives:
Dextromethorphan hydrobromide, dextromethorphan, terbutalihe, terbutaline sulfate, ephedrine, ephedrine hydrochloride, salbutamol sulfate, salbutamol, isoproterenol hydrochloride, isoproterenol and isoproterenol sulfate.

(16) Sex Hormones:
Progesterone and estradiol.

(17) Antidepressants:
Doxepine

(18) Cerebral Circulatory Ameliorants:
Hydergine, ergotalkaloid and ifenprodil.

(19) Antiemetics and Antiulcerants:
Metoclopramide, cleboprid, domperidone, scopolamine and scopolamine hydrobromide.

(20) Biopharmaceuticals:
Polypeptides.

(21) Other
Fentanil, desmopressin, digbxin, 5-fluorouracil and mercaptopurine.

In the adhering pharmaceutical preparation of the present invention, the pharmaceutical preparation is contained within the range of preferably 0.1 to 40 wt %, and more preferably 2 to 30 wt %, in the gel self-adhesive layer. Two or more types of these pharmaceutical preparations may be used in combination according to the object of treatment, their action and so forth. In addition, as means of containing pharmaceutical preparation, a pharmaceutical solution may be mixed in advance into a liquid gel adhesive, and this mixed solution may be coated onto a support to form a self-adhesive layer containing pharmaceutical, or an amount of pharmaceutical preparation sufficient for percutaneous absorption may be contained in a self-adhesive layer either not containing pharmaceutical preparation or containing an insufficient amount of pharmaceutical preparation by a method such as impregnation, contact transfer or spraying. A suitable method can be selected and employed from known methods of the prior art corresponding to the physical properties and so forth of the pharmaceutical to be contained in this manner.

Since the gel adhesivelof the present invention can be gelled from the three components of (A), (B) and (C) without using a chemical crosslinking reaction, and it is able to contain a large amount of liquid component (C), it offers the advantages of not causing skin irritation when applied to body skin, and causing little separation of the corneal layer during removal. In addition, it is also possible to promote percutaneous absorption of the pharmaceutical contained in the gel self-adhesive layer depending on the type of liquid component (C) contained therein.

EMBODIMENTS

The following provides a more detailed explanation of the present invention through the following embodiments. Furthermore, "parts" and "%", in the embodiments refer to "parts by weight" and "percent by weight", respectively. In addition, "180 degree removal force", "tack", "cohesive strength" and "moisture permeability" in the embodiments are measured according to the methods described below, and those results are shown in Table 1.

(1) 180 Degree Removal Force

A test sample cut to a size of 12 mm wide and 50 mm long was affixed to a Bakelite plate. After going back and forth over the affixed test sample with a roller applying a load of 850 g, the test sample was allowed to stand undisturbed for 30 minutes in a constant temperature device at 37° C. The test sample was then removed from the Bakelite plate in the 180 degree direction at a rate of 300 mm/min, the removal force at that time was measured, and adhesive strength was indicated with that measured value.

(2) Tack

After the peripheral surface of a stainless steel rope having a diameter of 5.1 mm was brought into contact with the self-adhesive surface of a test sample cut to a size of 12 mm wide and 50 mm long for 1 second at a speed of 30 mm/min and under a load of 10 g, the required load was measured when the stainless steel rope was pulled away from the test sample at separation speed of 10 mm/sec, and tack was indicated with that measured value.

(3) Cohesive Strength

After measuring adhesive strength according to the measurement method of the above-mentioned section (1), a visual judgment was made as to whether or not all or a portion of the adhesive remained on the Bakelite plate.

(4) Moisture Permeability 26 g of calcium chloride were placed in the bottom of a glass weighting bottle having an inner diameter of 38 mm, the top opening was sealed by a test sample having a self-adhesive layer tightly attached to polyester elastomer non-woven cloth having water vapor permeability of 7100 g/m$^2$/day, and the portion of the test sample not opposing the opening of the glass weighting bottle was adhered and fixed with adhesive tape to create a gas-impermeable state. This weighting bottle was then allowed to stand for 3 hours in a constant temperature, constant humidity bath at 40° C. and 90% relative humidity followed by calculation of the amount of permeated moisture per 24 hours per 1 square meter of the moisture permeable surface of the test sample from the increase in mass of the above-mentioned weighting bottle. The moisture permeability of the test sample was then indicated by this calculated value.

EXAMPLE 1

56 g of alkyl polyacrylate ester copolymer produced from 90 parts of 2-ethylhexylacrylate, 7 parts of methyl methacrylate and 3 parts of acrylic acid (10 wt % ethyl acetate solution) and 30 g of glycerin were added to 14 g of aliphatic polyether polyurethane (Texin 5590, made by Bayer) obtained by a polyaddition reaction using as main ingredients isophorone diisocyanate for the isocyanate component and a mixture (1:1 molar ratio) of polytetramethylene glycol (number average molecular weight: 2000) and 1,6-hexanediol for the diol component (5 wt % chloroform solution), and resulting mixed solution was coated on a silicon-coated mold release film so that the thickness of the self-adhesive layer after drying was 30 μm followed by drying for 30 minutes at 60° C. to prepare a gel adhesive in the form of a self-adhesive layer. A substrate comprised of 3.5 μm PET film was affixed on the upper surface of the resulting self-adhesive layer to prepare adhesive tape. The resulting adhesive tape was cut into pieces measuring 12 mm×50 mm, the mold release film was removed to measure the adhesive force of the self-adhesive layer. Those results are shown in Table 1. The 180 degree removal force was 241 g and tack was 283 g, both indicating satisfactory results. Moreover, there was no residual adhesive observed. In addition, moisture permeability was also satisfactory at 1670 g/m$^2$/day. Based on these results, the gel preparation obtained using the gel adhesive of the present invention was confirmed to have suitable adhesive strength, to have ease of removal to an extent that does not damage the skit surface, to be useful as an adhesive material, to have high moisture permeability, and to be useful as an adhesive material for body skin.

EXAMPLE 2

Adhesive tape was fabricated in the same manner as Example 1. However, during preparation of adhesive, 20 g of poly(oxyethyleneoxypropylene)glycol (oxyethylene/oxypropylene ratio: 10/90 wt %, Asahi Denka Kogyo, Pluronic L-31) were added and mixed with 30 g of polyurethane and 50 g of the: alkyl polyacrylate ester copolymer described in Example 1. The test results are shown in Table 1.

EXAMPLE 3

Adhesive tape was fabricated in the 'same manner as Example 1. However, during preparation of adhesive, 24 g of isopropyl myristate and 12 g of polypropylene glycol (number average molecular weight: 2000) were added and mixed with 16 g of polyurethane and 48 g of the alkyl polyacrylate ester copolymer described in Example 1. The test results are shown in Table 1.

EXAMPLE 4

Adhesive tape was fabricated in the same manner as Example 1. However, during preparation of adhesive, 2 g of ketoprofen (10 wt % chloroform solution) were added and mixed with 30 g of polyurethane, 44 g of the alkyl polyacrylate ester copolymer described in Example 1, and 24 g of oleic acid to obtain a pharmaceutical-containing gel adhesive. The test results are shown in Table 1.

EXAMPLE 5

Adhesive tape was fabricated in the same manner as Example 1. However, during preparation of adhesive, 11 g of isopropyl myristate, 11 g of the polypropylene glycol described in Example 3 and 11 g of ketoprofen were added and mixed with 32 g of polyurethane and 35 g of the alkyl polyacrylate ester copolymer described in Example 1 to obtain a pharmaceutical-containing gel adhesive. The test results are shown in Table 1.

EXAMPLE 6

Adhesive tape was fabricated in the same manner as Example 1. However, during preparation of adhesive, 18 g of polyvinyl acetate copolymer produced from 27.5 parts of 2-ethylhexylacrylate, 70 parts of vinyl acetate and 2.5 parts of acrylic acid (40 wt % ethyl acetate solution), 25 g of isopropyl myristate, 20 g of the poly(oxyethyleneoxypropylene)glycol described in Example 2 and 10 g of ketoprofen were added and mixed with 27 g of polyurethane to obtain a pharmaceutical-containing adhesive. The test results are shown in Table 1.

COMPARATIVE EXAMPLE 1

Adhesive tape was fabricated in the same manner as Example 3. However, in preparing the adhesive, the amount used of alkyl polyacrylate ester copolymer was changed to 64 g and polyurethane was not added. The test results are shown in Table 1.

COMPARATIVE EXAMPLE 2

Adhesive tape was fabricated in the same manner as Example 1. However, in preparing the adhesive, 50 g of polyurethane and 50 g of the alkyl polyacrylate ester copolymer described in Example 1 were added and mixed. Since a liquid component (C) was not used, although the 180 degree removal strength was decreased in the resulting adhesive tape, tack also decreased and the adhesive tape was unsatisfactory as an adhesive material.

COMPARATIVE EXAMPLE 3

Adhesive tape having a pharmaceutical-containing self-adhesive layer was fabricated in the same manner as Example 5. However, in preparing the adhesive, the amount added of alkyl polyacrylate ester copolymer was changed to 67 g and polyurethane was not added. The test results are shown in Table 1.

COMPARATIVE EXAMPLE 4

Adhesive tape was fabricated in the same manner as Example 3. However, in preparing the adhesive, the amount added of alkyl polyacrylate ester copolymer was changed to 100 g and polyurethane, isopropyl myristate and polypropylene glycol were not added. The test results are shown in Table 1.

COMPARATIVE EXAMPLE 5

Adhesive tape having a pharmaceutical-containing self-adhesive layer was fabricated in the same manner as Example 6. However, in preparing the adhesive, the amount added of polyvinyl acetate copolymer was changed to 45 g and polyurethane was not added. The test results are shown in Table 1.

EXAMPLE 7

Adhesive tape was fabricated in the same manner as Example 1. However, during preparation of adhesive, 33.6 g of the polyvinyl acetate copolymer described in Example 6, 21 g of isopropyl myristate, 7 g of triacetine and 30 g of isosorbide dinitrate (40 wt % acetone solution) were added and mixed with 8.4 g of polyurethane to obtain a pharmaceutical-containing adhesive. In addition, the thickness of self-adhesive layer after drying was changed to 40 μm. The test results are shown in Table 1.

EXAMPLE 8

Adhesive tape was fabricated in the same manner as Example 1. However, in preparing the adhesive, that having for its main ingredients 4,4'-diphenylmethane diisocyanate for the isocyanate component and a mixture (1:1 molar ratio) of polytetramethylene glycol (number average molecular weight: 1000) and 1,4-butanediol for the diol component were subjected to a polyaddition reaction, and 40 g of the alkyl polyacrylate ester copolymer described in Example 1 and 46 g of isopropyl myristate were added and mixed with 14 g of the resulting aromatic polyurethane (Dow Chemical, Pellethane 2363-80AE) (5 wt % chloroform solution). The test results are shown in Table 1.

EXAMPLE 9

Adhesive tape was fabricated in the same manner as Example 8. However, in preparing the adhesive, 40 g of the polyvinyl acetate copolymer described in Example 6 and 36 g of 1,2-propanediol were added and mixed with 24 g of polyurethane. The test results are shown in Table 1.

EXAMPLE 10

Adhesive tape was fabricated in the same manner as Example 1. However, in preparing the adhesive, 32 g of the polyvinyl acetate copolymer described in Example 6 and 20 g of the poly(oxyethyleneoxypropylene)glycol described in Example 2 were added and mixed with 48 g of aromatic polyether polyester (5 wt % THF solution) obtained by using 29.9 wt % of terephthalic acid and 3.3 wt % of isophthalic acid for the dicarboxylic acid component, and using 13.1 wt % of 1,4-butanediol and 53.7 wt % of polytetramethylene glycol (number average molecular weight: 1000) for the diol component. The test results are shown in Table 1.

EXAMPLE 11

Adhesive tape was fabricated in the same manner as Example 1. However, in preparing the adhesive, 42 g of the polyvinyl acetate copolymer described in Example 6 and 30 g of 1,2-propanediol were added and mixed with 28 g of aromatic polyether polyester (5 wt % chloroform solution) obtained by using 22.3 wt % of terephthalic acid for the dicarboxylic acid component, and using 9.0 wt % of 1,4-butanediol and 68.7 wt % of polytetramethylene glycol (number average molecular weight: 2000) for the diol component. The test results are shown in Table 1.

TABLE 1

| Example No. | Elastomer component (A) content (wt %) | Self-adhesive polymer component (B) content (wt %) | Liquid component (C) content (wt %) | Pharmaceutical content (wt %) | 180 degree removal force (g) | Cohesive force | Tack (g/5.1 mmφ) | Moisture permeability (g/m$^2$/day) |
|---|---|---|---|---|---|---|---|---|
| Ex. 1 | A (14) | AE (56) | GC (30) | 0 | 241 | ○ | 283 | 1670 |
| Ex. 2 | A (30) | AE (50) | POA (20) | 0 | 63 | ○ | 358 | 1230 |
| Ex. 3 | A (16) | AE (48) | IPM (24) PPG (12) | 0 | 57 | ○ | 236 | — |
| Ex. 4 | A (30) | AE (44) | OA (24) | KP (2) | 192 | ○ | 296 | — |
| Ex. 5 | A (32) | AE (35) | IPM (11) PPG (11) | KP (11) | 104 | ○ | — | — |
| Ex. 6 | A (27) | VA (18) | IPM (25) POA (20) | KP (10) | 73 | ○ | — | — |
| Ex. 7 | A (8.4) | VA (33.6) | IPM (21) TA (7) | ISDN (30) | 133 | ○ | — | — |
| Ex. 8 | B (14) | AE (40) | IPM (46) | 0 | 151 | ○ | — | — |
| Ex. 9 | B (24) | VA (40) | PG (36) | 0 | 177 | ○ | — | — |
| Ex. 10 | C (48) | VA (32) | POA (20) | 0 | 135 | ○ | — | — |
| Ex. 11 | D (28) | VA (42) | PG (30) | 0 | 291 | ○ | — | — |
| Comp. Ex. 1 | 0 | AE (64) | IPM (24) PPG (12) | 0 | 163 | × | — | — |
| Comp. Ex. 2 | A (50) | AE (50) | 0 | 0 | 76 | ○ | 127 | 570 |
| Comp. Ex. 3 | 0 | AE (67) | IPM (11) PPG (11) | KP (11) | 8 | × | — | — |
| Comp. Ex. 4 | 0 | AE (100) | 0 | 0 | 490 | ○ | — | — |
| Comp. Ex. 5 | 0 | VA (45) | IPM (25) POA (20) | KP (10) | 35 | × | — | — |

[Legend]
Elastomer component (A):
A = Polyether polyurethane (Texin 5590)
B = Polyether polyurethane (Pellethane 2363)
C = Polyether ester 1
D = Polyether ester 2
Self-adhesive polymer component (B):
AE = Alkyl polyacrylate ester copolymer
VA = Polyvinyl acetate copolymer
Liquid component (C):
GC = Glycerin
POA = Polyoxyethylene polyoxypropylene glycol
IPM = Isopropyl myristate
PPG = Polypropylene glycol
OA = Oleic acid
TA = Triacetine
PG = 1,2-propanediol
Pharmaceuticals:
KP = Ketoprofen
ISDN = Isosorbide dinitrate
Cohesive strength:
○: Adherence of adhesive on the Bakelite plate after the removal test was not observed.
×: Adherence of adhesive on the Bakelite plate after the removal test was observed.

EXAMPLE 12

The adhesive tape having a pharmaceutical-containing self-adhesive layer fabricated in Example 6 was punched out in the shape of a circle having a diameter of 16.5 mm to prepare the test piece. This was then affixed to the donor side of a snake skin (blue-green snake) installed on a vertical diffusion cell. The acceptor side was filled with 20 ml of pH 7.4 phosphate buffer solution. The diffusion cell was placed in a constant temperature bath at 37° C., and the phosphate buffer solution was stirred with a magnetic stirrer. After 6 hours, the phosphate buffer solution on the acceptor side was sampled, and the concentration of pharmaceutical was analyzed by liquid chromatography to measure the permeated amount of pharmaceutical. The permeated amount of pharmaceutical (ketoprofen) of this test piece was satisfactory at 18.1 μg/cm$^2$/6 hr (mean value of four permeability tests).

COMPARATIVE EXAMPLE 6

The permeated amount of pharmaceutical was measured in the same manner as Example 12. However, the adhesive tape of Example 6 was modified, and instead an adhesive tape was used that did not contain liquid component (C) (isopropyl myristate and poly(oxyethyleneoxypropylene) glycol). The amount of permeated pharmaceutical of this adhesive tape was 7.9 μg/cm$^2$/6 hr, equivalent to less than half of the amount in the case of containing liquid component (C) (Example 6).

INDUSTRIAL UTILIZATION

The gel adhesive of the present invention strongly adheres to the adhered surface; and particularly the surface of body skin, and can be easily removed without causing damage to the skin surface, while also not remaining on the skin surface. Thus, the gel adhesive of the present invention is useful in, for example, various types of adhesive materials and adhering pharmaceutical preparations.

What is claimed is:

1. A gel adhesive containing an elastomer component (A) comprising at least one elastomer selected from the group consisting of polyurethane elastomers, polyester elastomers and polyamide elastomers; a self-adhesive polymer component (B) compatible with said elastomer component (A) comprising at least one polymer selected from the group consisting of acrylate ester polymers comprising 50% by weight or more of an alkyl (meth)acrylate ester having 2 to 20 carbon atoms and 10% by weight or less of acrylic acid and vinyl acetate polymers comprising 50 % by weight or more of vinyl acetate and 10% by weight or less of acrylic acid; and, a liquid component (C) compatible with said elastomer component (A) and said self-adhesive polymer component (B) and comprising at least one compound selected from the group consisting of linolenic acid, linoleic acid, oleic acid, capric acid, isopropyl myristate, isooctyl palminate, ethyl oleate, diethyl sebacate, propylene glycol, hexanetriole, glycerin, polyethylene glycol, polypropylene glycol and poly(oxyethylene-oxypropylene) glycol, motoacetin, triacetin, triisooctanoate glycerin, sorbitan monocaprylate and sorbitan monooleate;

wherein the mixing weight ratio (B)/(A) of said self-adhesive polymer component (B) to said elastomer component (A) is from 1.0:2.0 to 1.0:0.1, and the mixing weight ratio [(A)+(B)]/(C) of the total weight of said elastomer component (A) and said self-adhesive polymer component (B) to said liquid component (C) is from 1.0:0.1 to 1.0:2.0; and, said adhesive gel is formed with said liquid component (C) being held in a mixture of said elastomer component (A) and said self-adhesive polymer component (B) without extruding.

2. An adhesive laminate comprising a support and a self-adhesive layer containing the gel adhesive according to claim 1 and formed and held on the support.

3. An adhesive laminate according to claim 2, wherein the self-adhesive layer further comprises at least one member selected from the group consisting of colorants, fragrances and refrigerants.

4. An adhering pharmaceutical laminate comprising a support and a self-adhesive layer formed and held on the support and containing the gel adhesive according to claim 1 and a pharmaceutical substance.

* * * * *